(12) United States Patent
Spinoza

(10) Patent No.: US 8,435,216 B2
(45) Date of Patent: May 7, 2013

(54) METHOD OF SECURING A LINE TO A PATIENT, FASTENERS, AND THEIR USE TO SECURE A LINE TO A PATIENT

(75) Inventor: Marc Howard Spinoza, Hertfordshire (GB)

(73) Assignee: Braidlock Limited, London (GB)

(*) Notice: Subject to any disclaimer, the term of this patent is extended or adjusted under 35 U.S.C. 154(b) by 0 days.

(21) Appl. No.: 12/838,236

(22) Filed: Jul. 16, 2010

(65) Prior Publication Data
US 2010/0305510 A1    Dec. 2, 2010

Related U.S. Application Data

(63) Continuation of application No. 09/506,361, filed on Feb. 18, 2000, now Pat. No. 7,766,880.

(30) Foreign Application Priority Data

Aug. 21, 1997 (GB) .................................. 9717821.4
Aug. 20, 1998 (WO) ...................... PCT/GB98/02502

(51) Int. Cl.
    *A61M 5/32* (2006.01)
(52) U.S. Cl.
    USPC ........... 604/174; 604/177; 604/178; 604/179; 604/180
(58) Field of Classification Search .................. 604/174, 604/177–180, 77–79; 87/2–5, 7–9, 12; 128/207.17
See application file for complete search history.

(56) References Cited

U.S. PATENT DOCUMENTS

| 656,187 | A | | 8/1900 | Gunnel ..................... 285/148.13 |
|---|---|---|---|---|
| 2,017,625 | A | | 10/1935 | Kellems ..................... 294/86.42 |
| 2,352,391 | A | * | 6/1944 | Kitselman ..................... 74/502.5 |
| 2,766,501 | A | | 11/1956 | Loyal ........................ 294/86.42 |
| 3,122,806 | A | | 3/1964 | Lewis ........................... 403/220 |
| 3,133,725 | A | | 5/1964 | Lanum ....................... 254/134.3 |
| 3,368,564 | A | | 2/1968 | Selix ............................. 604/180 |
| 3,487,837 | A | | 1/1970 | Petersen ....................... 128/349 |
| 3,672,006 | A | | 6/1972 | Fidych .......................... 24/122.6 |
| 3,883,102 | A | | 5/1975 | Trigg ............................... 248/75 |
| 3,907,003 | A | | 9/1975 | Regner et al. .............. 138/118.1 |
| 4,293,157 | A | | 10/1981 | Fidych ........................ 294/86.42 |
| 4,368,910 | A | | 1/1983 | Fidych ........................ 294/86.42 |
| 4,411,654 | A | | 10/1983 | Boarini et al. ........... 604/165.04 |
| 4,509,877 | A | * | 4/1985 | Sobin et al. ..................... 403/41 |
| 4,533,349 | A | | 8/1985 | Bark ............................. 604/174 |
| 4,545,322 | A | * | 10/1985 | Yang ............................... 188/67 |
| 4,604,821 | A | * | 8/1986 | Moser ......................... 43/44.98 |

(Continued)

FOREIGN PATENT DOCUMENTS

| DE | 19522301 | 1/1997 |
|---|---|---|
| EP | 0009893 | 4/1980 |

(Continued)

OTHER PUBLICATIONS

Office Communication, issued in United Kingdom Patent Application No. GB0514424.1, dated Mar. 10, 2010.

(Continued)

*Primary Examiner* — Quynh-Nhu H Vu
(74) *Attorney, Agent, or Firm* — Fulbright & Jaworski L.L.P.

(57) ABSTRACT

Fastener for securing a tube to a patient having a sleeve of variable length capable when lengthened of gripping the tube.

21 Claims, 14 Drawing Sheets

U.S. PATENT DOCUMENTS

| | | | |
|---|---|---|---|
| 4,754,685 A | 7/1988 | Kite et al. | 87/9 |
| 4,865,583 A * | 9/1989 | Tu | 604/508 |
| 4,867,154 A | 9/1989 | Potter et al. | 128/207.17 |
| 4,893,543 A | 1/1990 | Phillips | 87/34 |
| 4,906,234 A | 3/1990 | Voychehovski | 604/79 |
| 5,038,663 A | 8/1991 | Plummer | 87/6 |
| 5,129,891 A | 7/1992 | Young | 604/533 |
| 5,147,322 A | 9/1992 | Bowen et al. | 604/180 |
| 5,152,298 A | 10/1992 | Kreyenhagen et al. | 607/116 |
| 5,188,101 A | 2/1993 | Tumolo | 128/207.18 |
| 5,191,903 A * | 3/1993 | Donohue | 128/879 |
| 5,201,357 A | 4/1993 | Kuhn et al. | 164/132 |
| 5,221,265 A | 6/1993 | List | 604/180 |
| 5,232,453 A | 8/1993 | Plass et al. | 604/180 |
| 5,257,975 A | 11/1993 | Foshee | 604/105 |
| 5,292,312 A | 3/1994 | Delk et al. | 604/180 |
| 5,344,406 A | 9/1994 | Spooner | 604/179 |
| 5,370,627 A | 12/1994 | Conway | 604/180 |
| 5,395,344 A | 3/1995 | Beisang et al. | 604/180 |
| 5,405,378 A | 4/1995 | Strecker | 623/1.12 |
| 5,437,650 A | 8/1995 | Larkin et al. | 604/536 |
| 5,451,203 A * | 9/1995 | Lamb | 602/36 |
| 5,476,493 A | 12/1995 | Muff | 607/119 |
| 5,480,203 A | 1/1996 | Favalora et al. | 294/86.42 |
| 5,505,117 A | 4/1996 | Dunlap et al. | 87/1 |
| 5,507,733 A | 4/1996 | Larkin et al. | 604/534 |
| 5,649,541 A * | 7/1997 | Stuckey | 128/880 |
| 5,662,616 A | 9/1997 | Bousuet | 604/175 |
| 5,743,885 A | 4/1998 | Hoerby | 604/180 |
| 5,800,543 A | 9/1998 | McLeod et al. | 623/13.2 |
| 5,836,913 A | 11/1998 | Orth et al. | 604/107 |

FOREIGN PATENT DOCUMENTS

| | | |
|---|---|---|
| EP | 0137880 | 4/1985 |
| EP | 0516876 | 12/1992 |
| EP | 1512640 | 3/2005 |
| GB | 2061372 | 5/1981 |
| GB | 1601334 | 10/1981 |
| JP | 55-16650 | 2/1980 |
| JP | 06-327776 | 11/1994 |
| JP | 10-248941 | 9/1998 |
| WO | WO 81/01519 | 6/1981 |
| WO | WO 82/03775 | 11/1982 |
| WO | WO 91/14034 | 9/1991 |
| WO | WO 92/06235 | 4/1992 |
| WO | WO 93/25264 | 12/1993 |
| WO | WO 95/29727 | 11/1995 |
| WO | WO 97/21459 | 6/1997 |
| WO | WO 99/10250 | 3/1999 |
| WO | WO 03/090835 | 11/2003 |
| WO | WO 03/105727 | 12/2003 |

OTHER PUBLICATIONS

"Communication pursuant to Article 96(2) EPC," Official action of the European Patent Office in European Application No. 04021343, dated Apr. 11, 2007.

Derwent Accession No. 95-129939/9517, "New born baby naval vein catheterisation device—has sleeve with cap on its non-working end and internal catheter duct," Abstract of Patent No. SU1836114, published Aug. 23, 1993.

Office Communication, issued in U.S. Appl. No. 09/506,361, dated May 22, 2002.

Office Communication, issued in U.S. Appl. No. 09/506,361, dated Aug. 1, 2002.

Office Communication, issued in U.S. Appl. No. 09/506,361, dated Apr. 8, 2003.

Office Communication, issued in U.S. Appl. No. 09/506,361, dated Jan. 9, 2004.

Office Communication, issued in U.S. Appl. No. 09/506,361, dated Mar. 12, 2004.

Office Communication, issued in U.S. Appl. No. 09/506,361, dated Jul. 13, 2005.

Office Communication, issued in U.S. Appl. No. 09/506,361, dated Dec. 1, 2005.

Office Communication, issued in U.S. Appl. No. 09/506,361, dated Jun. 5, 2006.

Office Communication, issued in U.S. Appl. No. 09/506,361, dated Nov. 29, 2007.

Office Communication, issued in U.S. Appl. No. 09/506,361, dated Jun. 24, 2008.

Office Communication, issued in U.S. Appl. No. 09/506,361, dated Dec. 29, 2008.

Office Communication, issued in U.S. Appl. No. 09/506,361, dated Jun. 11, 2009.

Office Communication, issued in U.S. Appl. No. 09/506,361, dated Mar. 25, 2010.

* cited by examiner

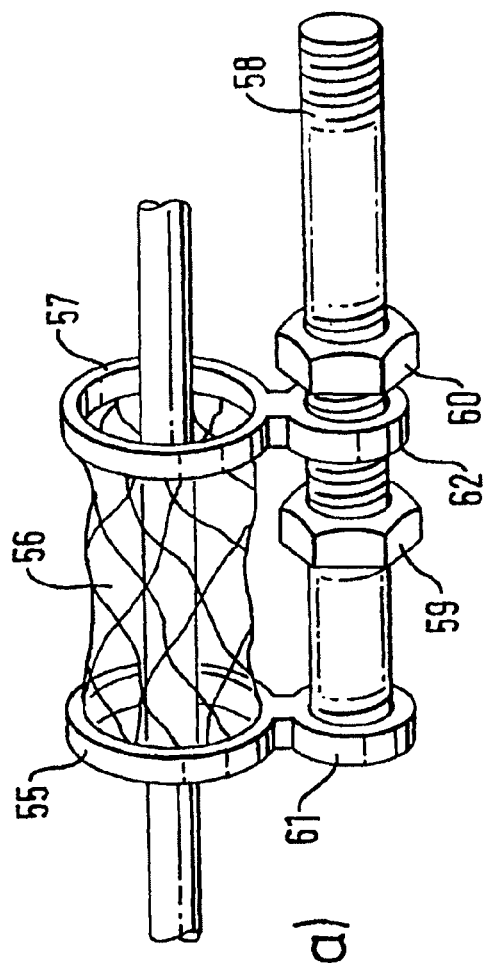
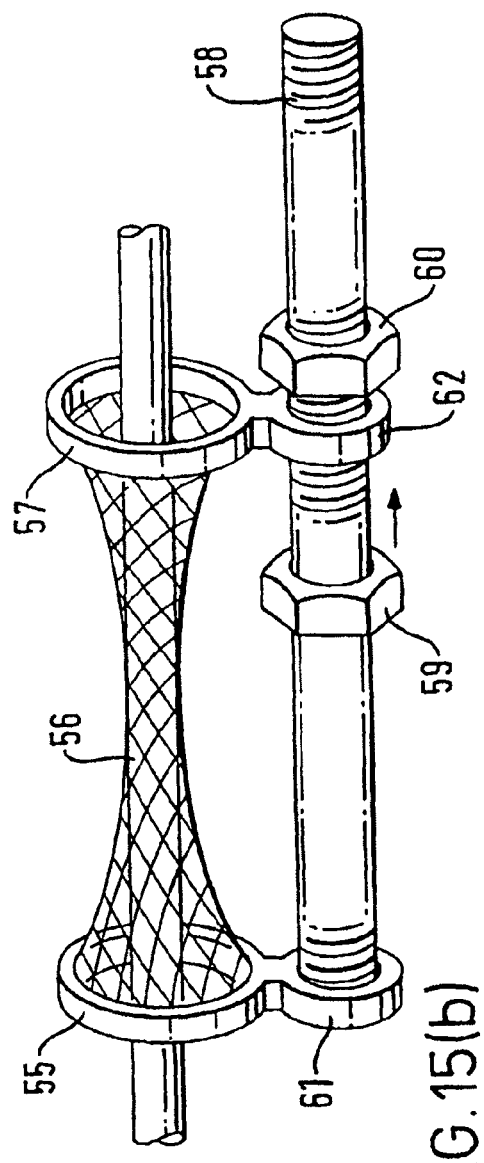
FIG.15(a)
FIG.15(b)

METHOD OF SECURING A LINE TO A PATIENT, FASTENERS, AND THEIR USE TO SECURE A LINE TO A PATIENT

RELATED APPLICATIONS

This application is a continuation of U.S. patent application Ser. No. 09/506,361, filed Feb. 18, 2000; which is a national phase application under 35 U.S.C. §371 of International Application No. PCT/GB98/02502, filed Aug. 20, 1998; which claims priority to United Kingdom Application No. 9717821.4, filed Aug. 21, 1997. The entire contents of all these applications are incorporated by reference.

DESCRIPTION

The present invention relates broadly to the field of fasteners and is particularly concerned with medical or surgical fasteners that secure tubes or other lines to a patient. In one example, the invention can be used to secure a catheter to a patient, for example to the patient's arm or umbilicus, and in another example the invention can be used to hold an endotracheal tube that ventilates a patient. The catheter application will be described first, with particular reference to the treatment of premature babies or of term babies requiring resuscitation measures. This field is the Applicant's speciality as a doctor, and is the origin of the present invention.

Catheters are long, thin, flexible tubes of plastics material that can be inserted into a blood vessel or other body cavity for introducing or removing fluids, either liquids or gases. They are used by medical personnel as a matter of routine. Catheters can vary widely in size, depending upon the application: from about 0.1 mm internal diameter for use with premature babies, up to more than 5 mm internal diameter for use with adults. They often have measurement markings provided along their length, the markings serving as a guide to the depth of insertion into the patient's body.

Premature infants, or term infants requiring resuscitation measures, invariably require the ongoing administration of drugs and fluids. Moreover, frequent blood samples must be taken to monitor the infant's progress, bearing in mind that infants can deteriorate very rapidly if things go wrong without being detected promptly. Clearly, therefore, it is vital that good venous/arterial access is achieved and maintained.

Venous/arterial access through peripheral access sites such as the arms, legs or scalp is to be avoided if at all possible. As infant patients can be so small, it is desirable to avoid puncturing their blood vessels even if suitable blood vessels can be found: peripheral access is usually very limited. Moreover, serious injury can ensue when administering certain drugs or fluids peripherally, ranging from superficial tissue damage to permanent disfigurement. Plastic surgery may be required for these peripheral injuries and, in later life, orthopaedic intervention may be required to treat damaged joints.

Conversely, the venous and arterial vessels found within the normal anatomy of an umbilical cord (i.e. at the umbilical stump or umbilicus) provide ready access to a infant's bloodstream and so are favoured over peripheral access sites. Accordingly, for those babies admitted to a neo-natal intensive care unit and unless complications arise which inhibit use of the umbilicus, the usual practice is to site small diameter umbilical catheters (also known as lines) in the umbilicus as soon as possible after birth. Once in situ, these lines readily allow fluids including transfusions and drugs to be administered and blood samples to be taken.

When locating a line inside an infant's body, a nurse or doctor has to be careful to place the line in a position that least compromises the dynamics of the cardiovascular system. This is a trial-and-error process, involving an attempt at correct positioning followed by an X-ray to confirm the actual position of the end of the line. At that stage, if the line is found to extend beyond its target position, it can be pulled back. On the other hand, if the line falls short of the target, the risk of introducing infection means that the line is never inserted any deeper. Instead, the original line is withdrawn and discarded and a sterile replacement line is sited: the positioning procedure begins allover again.

Clearly, once a line is in an acceptable position after this intricate positioning procedure, it is essential that the line is securely anchored to avoid any accidental displacement with respect to the infant's umbilicus. The line may need to be in place for a period of weeks: the longer a line remains undisturbed in situ in accordance with planned treatment, the lower the risk of harm to the patient. With premature infants in particular, lines are essential: if access via them is lost, the risk of a poor outcome or even death is notably higher. Dislodgement of a line is most undesirable because reinsertion not only increases the risk of introducing infection, but also is difficult to achieve because the anatomy of the umbilicus naturally becomes distorted and/or tends to close up tightly a few days after birth.

The current and long-standing line-anchoring practice is to suture the line directly to the umbilicus and then to construct a securing bridge from medical adhesive tape applied to the abdomen. This adhesive tape bridge takes the stress of axial loads on the line at points spaced from the umbilicus, thereby minimising disturbance to the umbilicus.

In a common construction illustrated in FIG. 1, an adhesive tape bridge 10 is made from a total of six strips of medical adhesive tape. Two pairs of strips are adhesively secured to the baby's abdomen 11 one each side of, and spaced from, the umbilicus 12. Each pair is shaped into an inverted V and the pairs are mutually parallel with their apices aligned with the umbilicus, creating upstanding supports. The remaining two strips of tape are applied face-to-face about the line 13 and their ends are attached to the apices of the supports, thus bridging the gap between the supports and gripping the line 13. Alternatively, the strips of adhesive tape gripping the line 13 may be sutured to the baby's abdomen 11, avoiding sticking extra strips of adhesive tape to the abdomen.

The adhesive tape bridge is cheap and simple but suffers a number of problems. Perhaps most seriously, and no matter how carefully an adhesive tape bridge is constructed, the adhesive will deteriorate over time. The bridge may ultimately fall apart or otherwise fail to grip the line, thus presenting a danger of the line being displaced. Clearly, this risk increases the longer an adhesive tape bridge is relied upon: it must be inspected frequently and if necessary renewed. Of course, inspection and renewal are operations that can themselves disturb the line.

If an adhesive tape bridge fails to grip a line, the line can be pulled out or otherwise displaced from its ideal location by movements of the infant, as well as by disturbances when medical personnel carry out clinical procedures on the infant such as re-intubation, taking samples, changing nappies/diapers, cleaning and so on. Paradoxically, any disturbance of the line can be hidden by the bulky adhesive tape bridge and so escape detection, especially as more tape may have been added over time to repair damage to the bridge. Wholly unnecessary death or disability is the all too frequent result.

The infant's movements and the disturbance of clinical procedures can, of course, also contribute to the deterioration of the adhesive tape bridge. However, the main factor in deterioration stems from the fact that a premature infant's skin is immature, undeveloped and hence very permeable. Coupled with an infant's large surface area to weight ratio, this leaves the infant liable to dehydration. This is the reason why premature infants are kept in a humidified atmosphere within incubators or bubble coverings. Over time, the moisture promoted by these humid surroundings can weaken the bonds that hold together an adhesive tape bridge and that hold the bridge in place on an infant's skin.

Other disadvantages of the adhesive tape bridge are that adhesive contact with a premature infant's abdomen could damage the infant's extremely fragile and sensitive skin, and that its construction takes valuable time.

Some of the shortcomings of adhesive tape bridges are addressed in U.S. Pat. No. 5,370,627 to Conway. Conway discloses a catheter securing bridge that consists of an annular base having a central aperture and two semi-circular flaps pivotally connected to the base. The underside of the base is coated with an adhesive layer, as are the opposing faces of the flaps.

In use, the base is adhesively secured to the infant so that it encircles the umbilicus which is thus presented in the middle of the aperture. Next, the catheter is introduced into the umbilicus, and once properly located is sutured in place on the umbilicus. The flaps are lifted up towards one another so that they extend upwardly from the base and are then adhesively secured together, trapping a portion of the projecting catheter.

Whilst Conway's catheter securing bridge represents an improvement over the conventional adhesive tape bridge in terms of convenience of application, it is apparent that Conway has taken the adhesive tape bridge as a starting point. Conway's device therefore shares many of the problems suffered by the adhesive tape bridge: in particular, it will eventually work loose and will therefore allow the catheter to become displaced, and it can damage the patient's skin by virtue of adhesive contact.

Neonatal care requires exceptional precision but, of course, it is not the only medical or surgical field that requires reliable and convenient location of a catheter. Intravenous drips, chest and abscess drains and urethral catheters, are merely examples of many other applications that would benefit from better fasteners.

Analogous problems are experienced in fastening an endotracheal tube used to ventilate a patient: see FIG. 2. When intubating the patient 14, the endotracheal tube 15 is passed through a plastics grip or, as illustrated, a silicone rubber collar 16 held on the patient's mouth by a net or stocking hat and ribbon ties as shown that pass through holes 17 in the collar 16, and is fixed to the collar 16 by a cable tie 18 or suture (not shown). The patient 14 is then x-rayed to ensure that the end of the endotracheal tube 15 is correctly positioned just above the bifurcation of the trachea, i.e. the point where the trachea branches into the bronchi. If the endotracheal tube 15 is not correctly positioned—and adjustment is usually required—the cable tie 18 or suture must be removed, the tube 15 pulled out or pushed in (the risk of infection is acceptable in this instance because the trachea is always exposed to the environment), the cable tie 18 or suture must be re-affixed and then another x-ray must be performed to confirm correct positioning. Repeated removal and replacement of the cable tie 18 or suture takes time, costs money and generally militates against correct positioning of the endotracheal tube 15.

It is essential that the endotracheal tube is accurately positioned so as to avoid injury at the bifurcation of the trachea or inadvertent ventilation of only one side of the chest, usually the right side because the right bronchus is anatomically more vertical compared to the left bronchus.

In general, the problems of fastening lines and other articles to a patient are well known and have been addressed by numerous inventors. Examples of recent thinking are U.S. Pat. No. 5,152,298 to Kreyenhagen et al, U.S. Pat. No. 5,257,975 to Foshee, and U.S. Pat. No. 5,662,616 to Bousquet.

Kreyenhagen et at discloses an implantable suture sleeve for anchoring the lead body of an implantable medical device, such as a cardiac pacemaker, to a patient's body tissue such as a vein and/or a muscle within the chest cavity. The sleeve includes an elongated externally threaded tubular member having a lumen for receiving the lead body and an internally-threaded collar that is threaded onto the external thread of the tubular member. The tubular member and the collar have engaging tapered surfaces so that, when the collar is tightened, a soft insert within the tubular member is compressed into gripping engagement with the lead body.

As the suture sleeve of Kreyenhagen et al. is designed for implantation, it is clearly intended for once-only operation. Further, as a result of its specialised purpose, the suture sleeve is unnecessarily bulky, expensive and complex, both in its design and its operation, for the more general purposes of the present invention. It will also be noted that the suture sleeve exerts its inward compressive force on the lead body about a narrow annular ridge or band and so is designed to crush the lead body to a limited extent. It is noted that crushing is not appropriate for a tubular lines as this would restrict its lumen. It is also noted that the facility for limiting the extent of crushing requires the further complication of cooperable surfaces on the tubular member and the collar.

Foshee discloses a cannula retention device actuable in a single operation to secure a cannula above and below a patient's body wall. The embodiments disclosed include a tubular sleeve which is slit either longitudinally or, preferably, spirally. The sleeve is secured to the distal end of the cannula while being mounted loosely over the cannula at the proximal end. Longitudinally compressing or twisting the sleeve, as appropriate, makes the slit tubing expand above and below the body wall to secure the cannula.

It will be noted that the means of location disclosed in Foshee requires modification to the article to be attached to the patient, in this case a cannula, and would be of no use in attaching an article at points of attachment outside the body wall.

Bousquet was published after the priority date of the present invention and discloses a transcutaneous access device including a subcutaneous skirt, a transcutaneous neck and an extracutaneous bellows-like extendible sleeve. The device functions as a conduit for an access catheter and is sized to minimise contact with the catheter. The aim is to allow motion of the catheter relative to the implanted portions of the access device so that the patient's body motion does not break the biological seal that forms around the access device. Allowing motion of, and avoiding contact with, the catheter in this way is contrary to the aims of the present invention.

It is against this background that the invention has been devised.

From one aspect, the invention resides in a method of securing a line to a patient or of adjusting the position of a line thus secured, comprising elongating and narrowing a sleeve applied to the line to grip the line and resist movement of the line along its longitudinal axis with respect to the sleeve.

Analogously, the invention encompasses a fastener for securing a line to a patient comprising a sleeve of variable length capable when lengthened of gripping the line.

The invention has many benefits. It provides a simple, cheap and effective solution to the problem of securing lines to a patient, especially to a premature infant in moistureridden environments. The sleeve of the invention can be so cheap as to be disposable without undue cost. The invention provides versatility, flexibility and adjustability, although it can as easily be permanently fixed. The invention prevents repeated, unnecessary, painful and invasive procedures, for example, re-siting cannulas that have become displaced. Most importantly therefore, the invention avoids injury to a patient and indeed can be expected to save many lives.

Preferably, after first gripping the line, the sleeve elongates in response to movement of the line and resists continuance of that movement. This provides a locking effect.

To allow adjustment, the method of the invention may further comprise shortening and widening the sleeve to release the line and permit movement of the line. Advantageously, the sleeve can be shortened by pushing its ends towards one another. Thus shortened, the sleeve is capable of sliding along the line.

The line may be passed out of the sleeve through a wall of the sleeve, and further may be passed back into the sleeve through the wall of the sleeve. In this way, the line can be led to wherever it may be needed with respect to the sleeve, and can be used to create loops in the sleeve for attachment purposes.

The invention allows a method of securing the line, checking the position of the line with respect to the patient by X-ray or other means, adjusting the line into a desired position, and locking it in the desired position. If desired, locking can be achieved by adhesively connecting the line and the sleeve, which could be by the application of an adhesive compound, or of an adhesive tape.

The fastener of the invention may be attached to a patient by any of the conventional methods employed in securing medical lines e.g. tape, bandage, suture or Velcro (trade mark) hook-and-eye fastening material.

The fastener preferably includes a suitable attachment means for attaching the sleeve to a patient. For example, the attachment means may comprise one or more loops, which may be formed by doubling over the sleeve or by passing the line through a wall of the fastener.

Alternatively, the attachment means may comprise an adhesive pad, or a flap of material such as a flare or flange which is then sutured to the patient.

Further to reduce the reliance upon adhesive, the attachment means advantageously comprises a harness, sling or other means adapted to embrace a part of the patient. Alternatively, the fastener may be sutured directly to the patient.

The fastener of the invention can comprise a support such as the body of a collar for an endotracheal tube, together with movable means for varying the length of the sleeve with respect to the support. To provide a measure of self-locking, the movable means preferably includes bias means acting to elongate the sleeve. Conveniently, the movable means includes at least one lever acting upon the sleeve which may be a finger tab movable against the bias means to shorten the sleeve.

The fastener may further comprise holding means for holding the movable means in a position in which the sleeve grips the line. To this end, the movable means may incorporate a locking mechanism. This can be embodied in many ways but one way is to move means such as a nut along a threaded rod and to employ a second nut also threaded on the rod to lock the first nut.

For optimum flexibility, the sleeve preferably has a perforated or foraminous wall defining a plurality of openings. An opening may be capable of permitting the line to pass through the wall of the sleeve.

To this end, the sleeve wall is preferably a mesh, grid, net or web and may be of filamentary construction such as a spirally woven tube.

The sleeve is preferably radio-opaque, thereby serving as a marker on X-ray images. This provides useful information when identifying the amount of line lying within and outside the patient on an X-ray image. Current practice is to place a metal pointer, such as a needle, near to the point of interest, e.g. entry of the line, to identify that point. The degree of radio-opaqueness of the sleeve may also be selected to distinguish one line from another on an X-ray image where one or more similar lines are attached to a patient. A selection of sleeves having different and respectively unique radio-opaque indicia would achieve the same objective.

In order that the invention can be more readily understood, reference will now be made, by way of example only, to the accompanying drawings in which.

Figure 2:
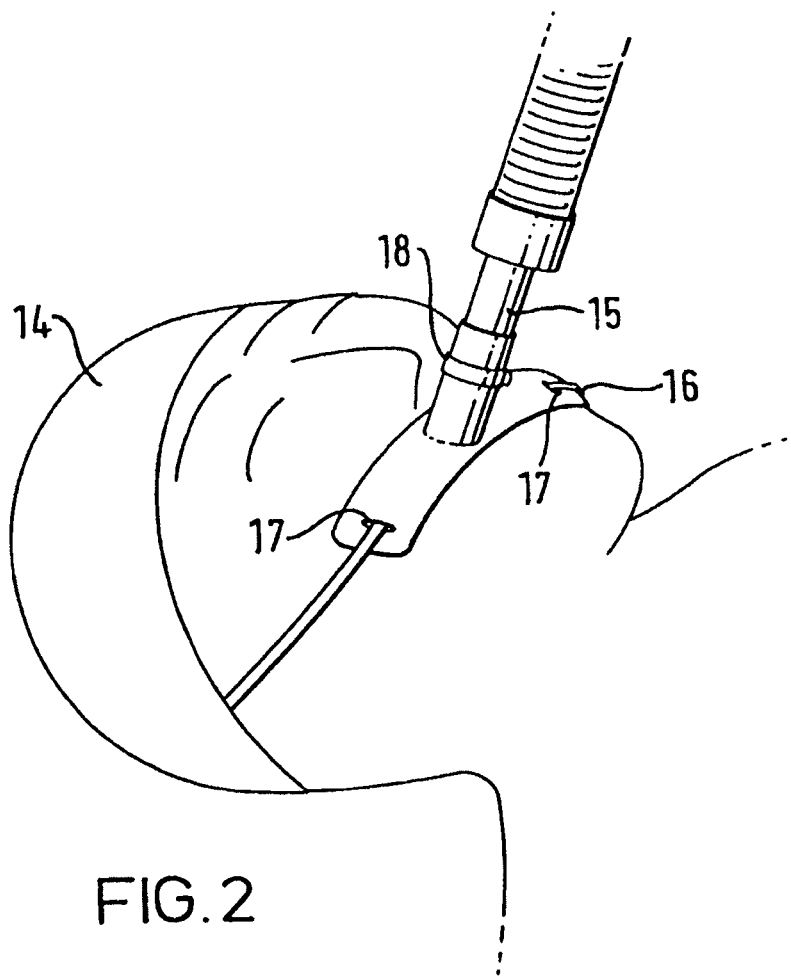
FIG. 2 is a schematic perspective view of a prior art technique for securing an endotracheal tube to a patient, using a cable tie or suture to attach the tube to a collar.
Figure 3:
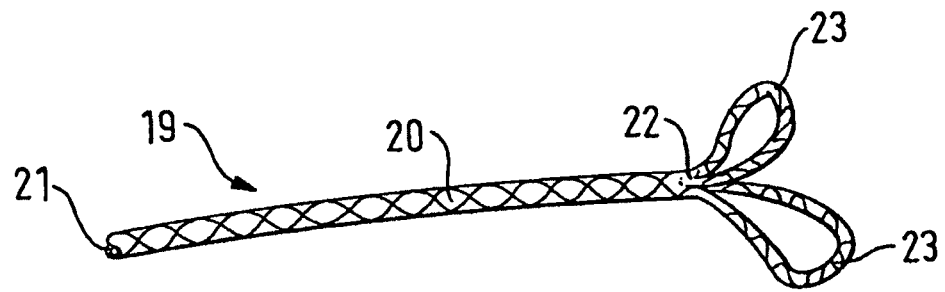
FIG. 3 is a schematic side view of a fastener constructed in accordance with the invention.
Figure 4A:
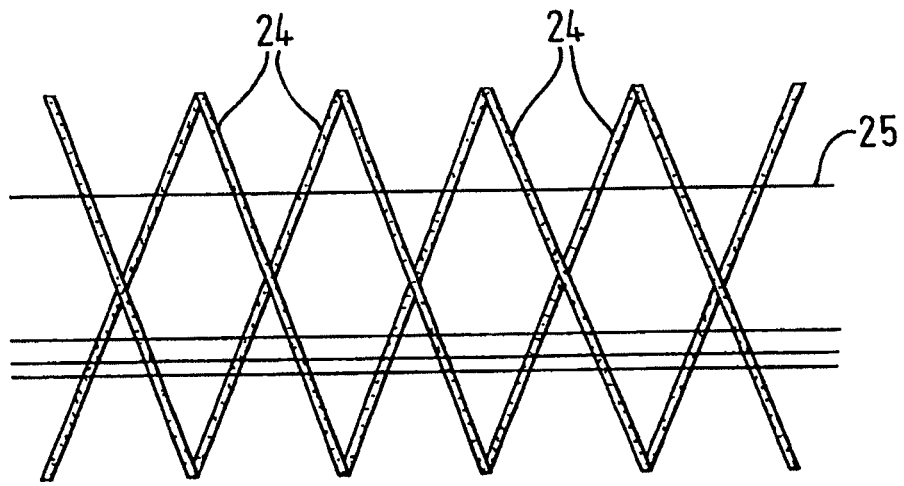
Figure 4B:
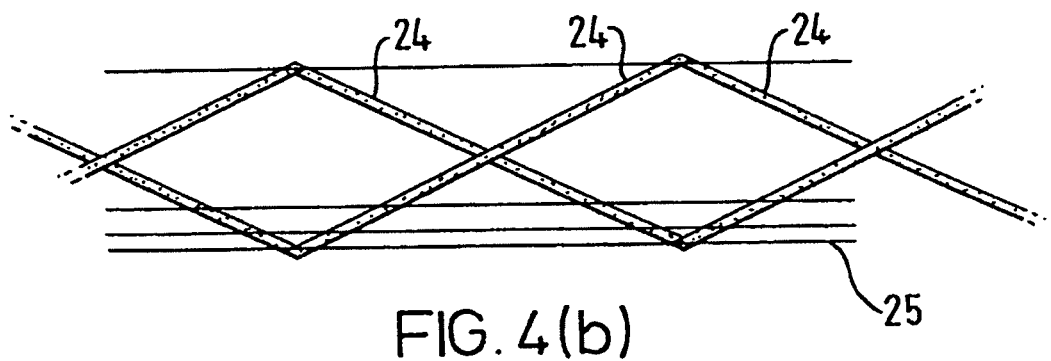
Figure 6:
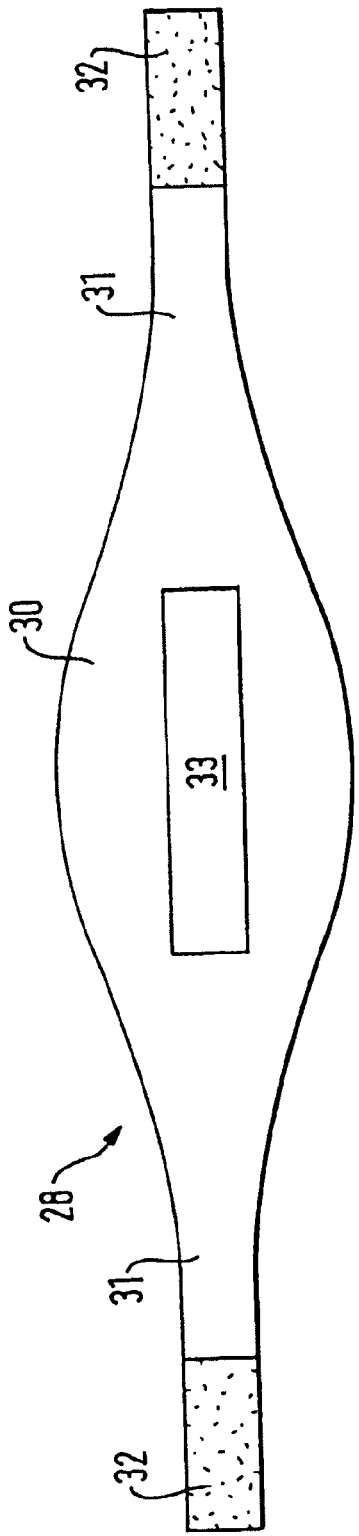
Figure 7:
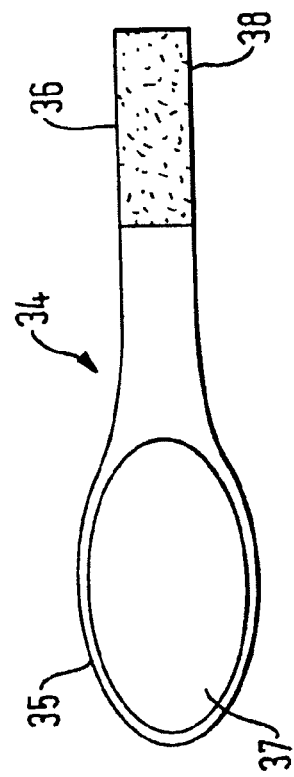
Figure 8:
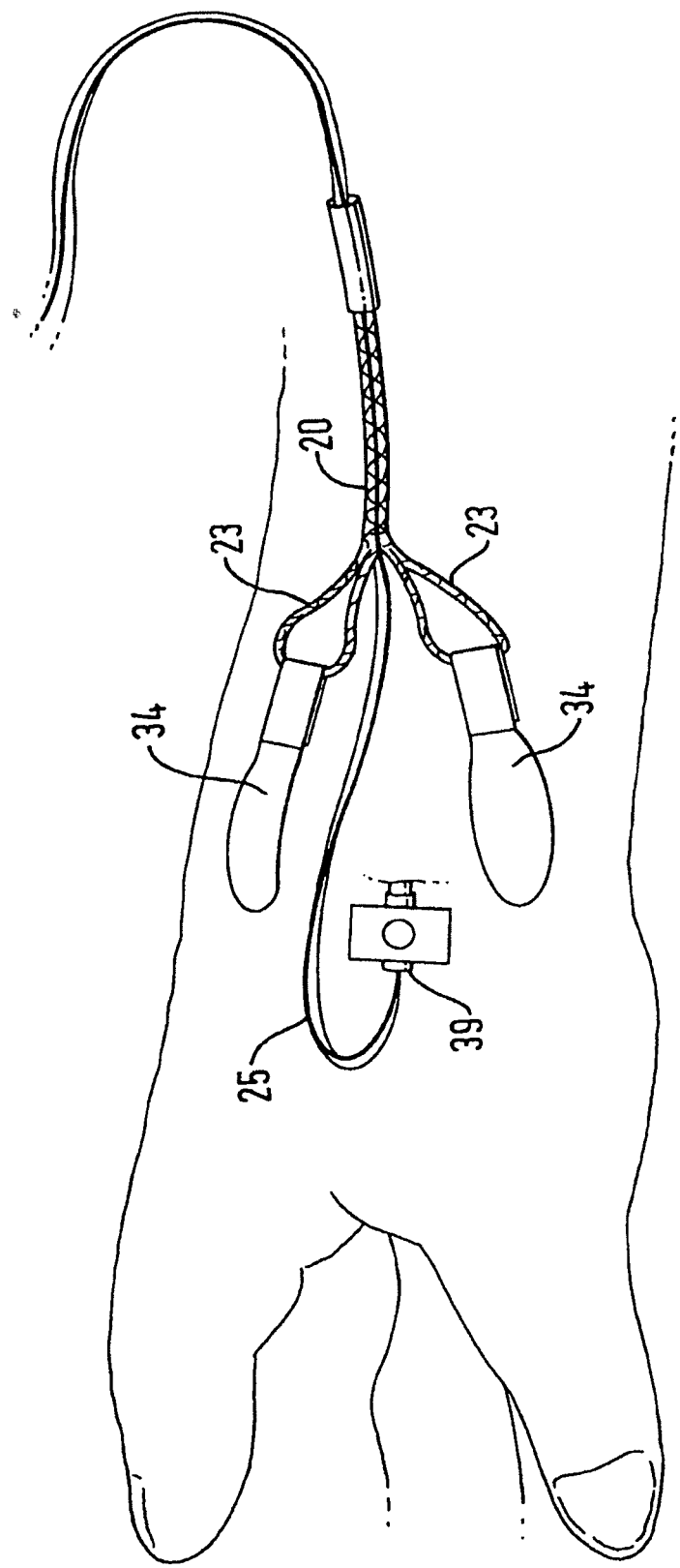
Figure 9:
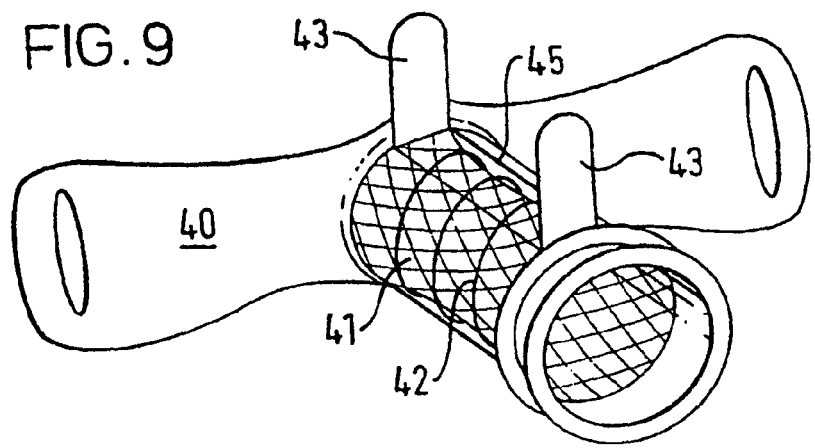
Figures 10A, 10B, 10C:
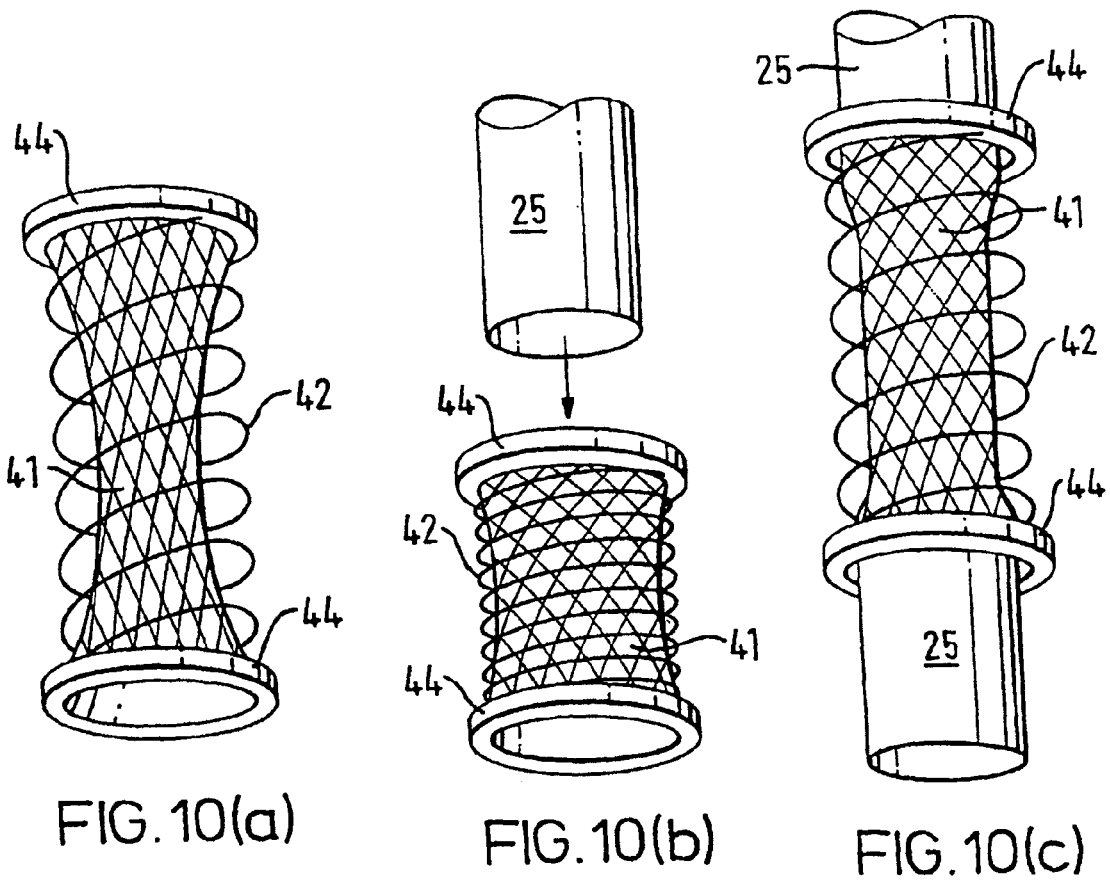
Figure 11A:
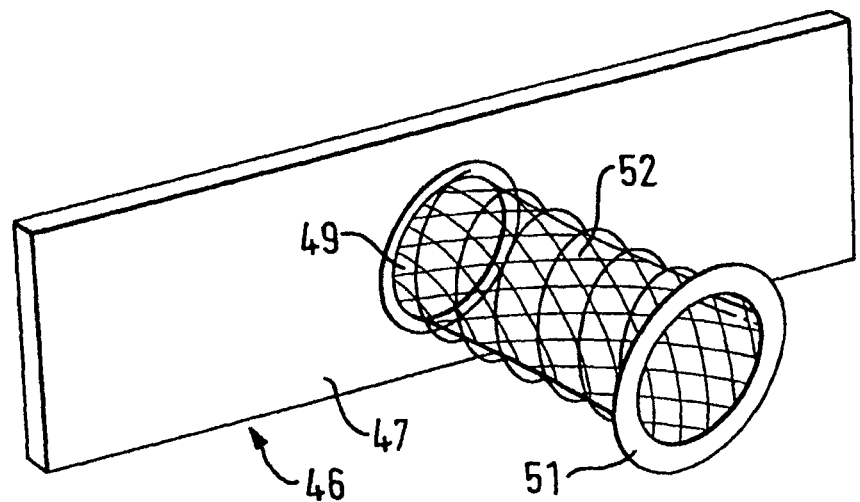
Figure 11B:
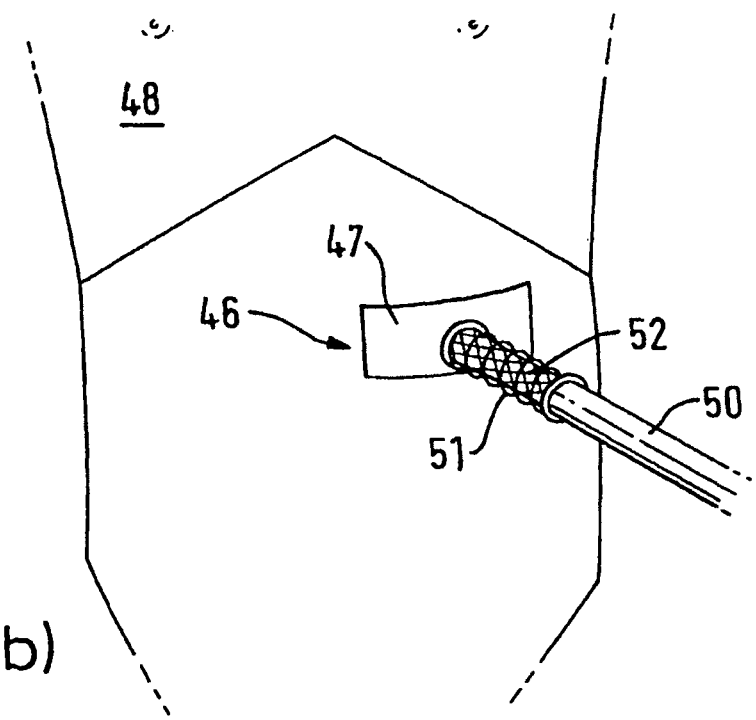
Figure 12:
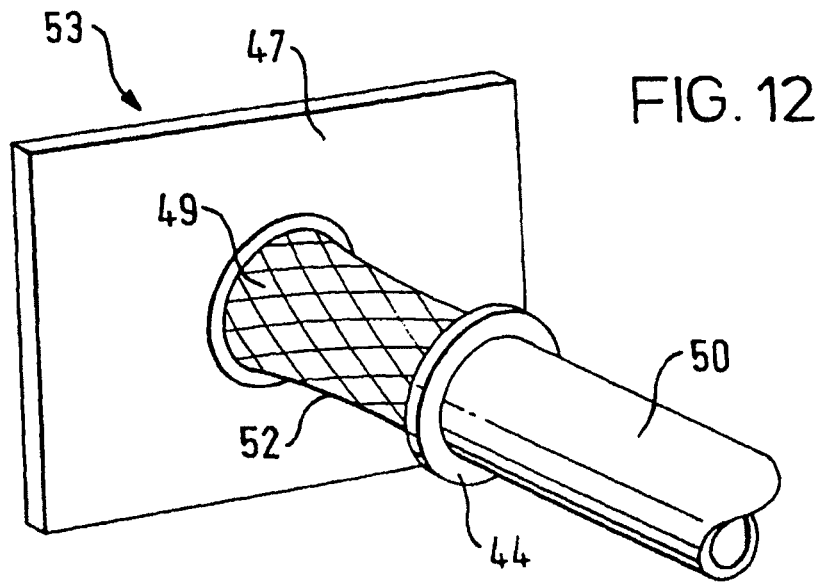
Figure 13:
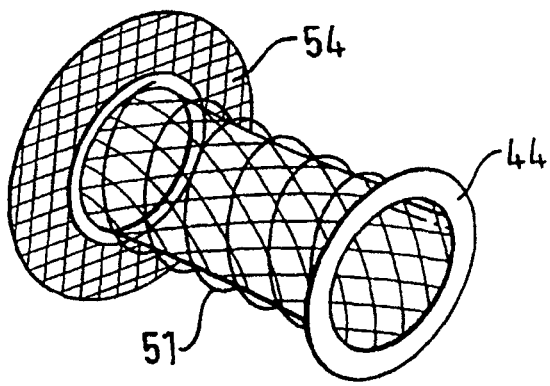
Figure 14:
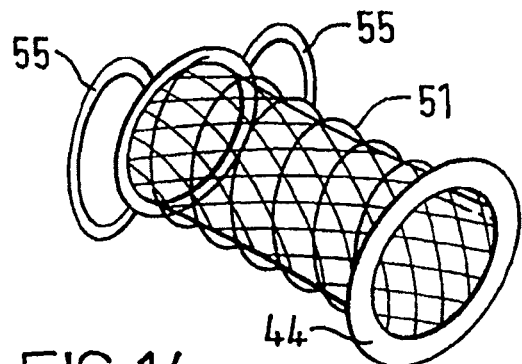
Figure 16A:
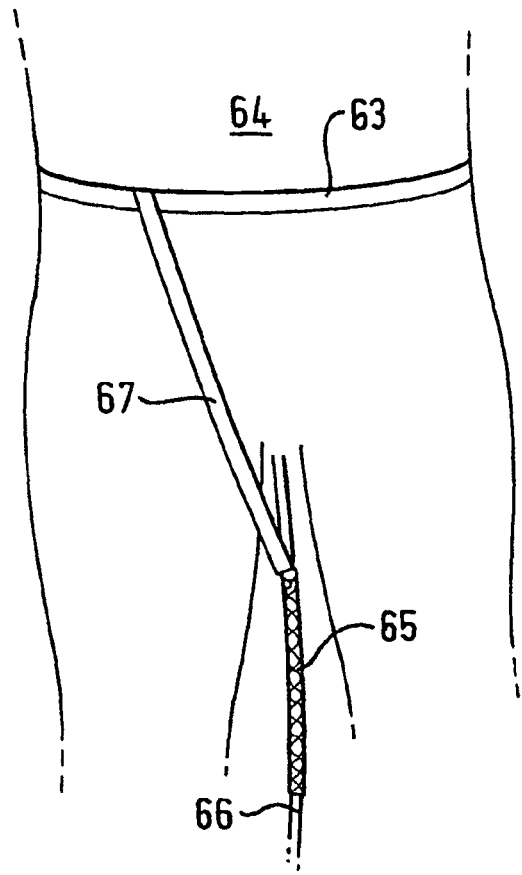
Figure 16B:
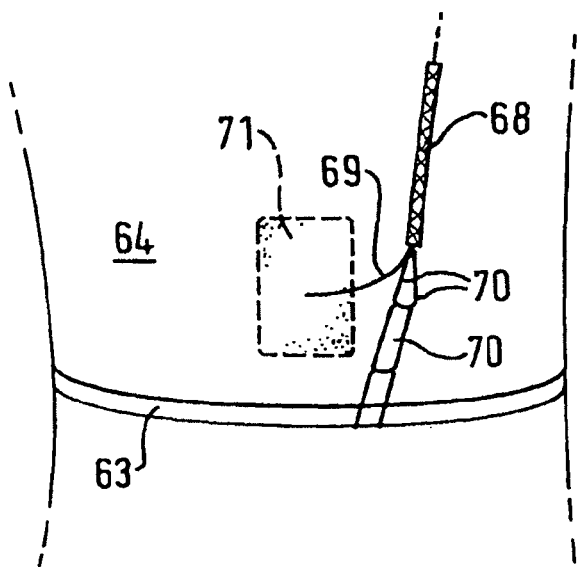
Figure 17A:
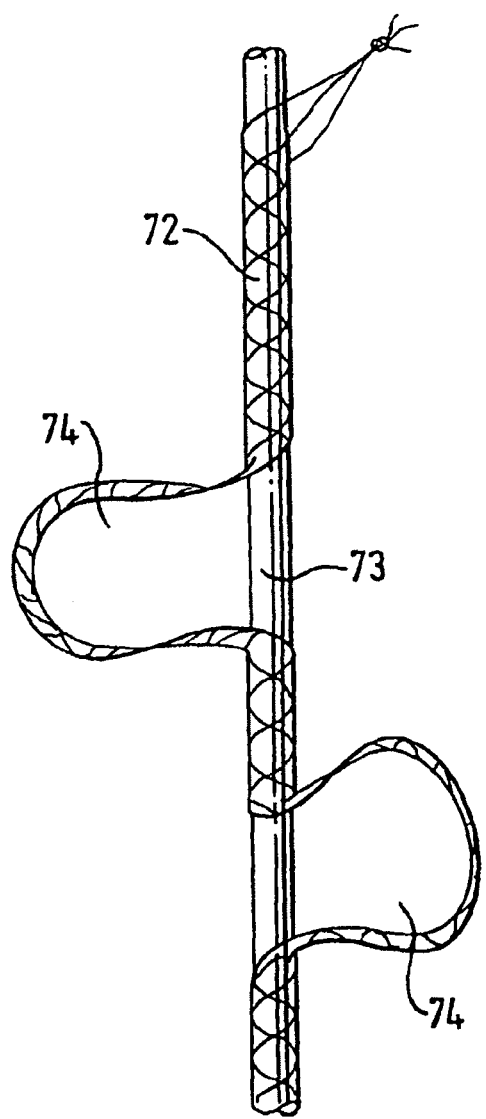
Figure 17B:
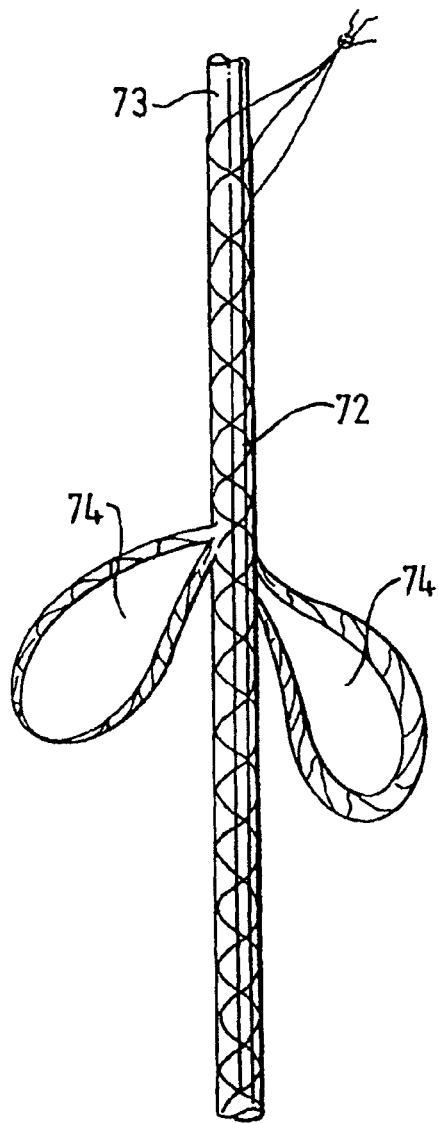

FIGS. 4(a) and 4(b) are schematic side views illustrating the response of the fastener of FIG. 3 to longitudinal compression and tension respectively;

FIGS. 5(a) to 5(l) diagrammatically illustrate a series of steps in applying the fastener of FIG. 3 to an umbilical line;

FIG. 6 is a schematic plan view of a harness for use with the invention;

FIG. 7 is a schematic plan view of an adhesive tab for use with the invention;

FIG. 8 is a schematic perspective view of the adhesive tab of FIG. 7 and the fastener of FIG. 3 in use together on a patient;

FIG. 9 is a schematic perspective view of a collar employing the invention to secure an endotracheal tube to a patient instead of the cable tie or suture used previously as in FIG. 2;

FIGS. 10(a), 10(b) and 10(c) are schematic perspective views of a sleeve and biasing means forming part of the collar shown in FIG. 9;

FIGS. 11(a) and 11(b) are schematic perspective views of an embodiment of the invention employing an adhesive pad and including biasing means on the pad acting on the sleeve, FIG. 11(a) showing the fastener in isolation and FIG. 11(b) showing the fastener in use attaching a catheter or drain to a patient;

FIG. 12 is a schematic perspective view of an embodiment corresponding to that illustrated in FIG. 11(a) but without the biasing means;

FIG. 13 is a schematic perspective view akin to the embodiment of FIG. 11(a) but with the adhesive pad replaced by an annular flare or flange of material for suturing the fastener to the patient;

FIG. 14 is a schematic perspective view akin to the embodiment of FIG. 13 but with the flare or flange of material replaced by loops for securing the fastener to a patient by means of a harness;

FIGS. 15(a) and 15(b) are schematic perspective views of an embodiment in which movable means acting on the sleeve can be held by holding means when the sleeve is extended, FIG. 15(a) showing the sleeve when contracted and FIG. 15(b) showing the sleeve when extended;

FIGS. 16(a) and 16(b) are detail views illustrating further uses of the invention which employ a supporting belt around a patient's torso, FIG. 16(a) showing the fastener holding a urinary catheter and FIG. 16(b) showing the fastener holding an epidural line; and FIGS. 17(a) and 17(b) are schematic side views of alternative loop-forming techniques.

Figure 1:
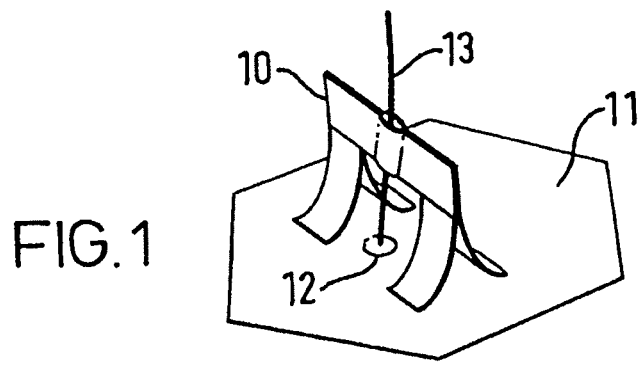
FIG. 1 is a schematic perspective view of a prior art technique for securing a line to the umbilicus of a premature infant, using an adhesive tape bridge.

Reference has already been made to FIGS. 1 and 2 in the foregoing discussion of the prior art. Referring then to FIG. 3, a fastener 19 constructed in accordance with the present invention includes a generally tubular sleeve 20 defined by helically-wound and interwoven or intertwined filaments of nylon. The wall of the sleeve 20 may therefore be described as a braid or plait of foraminous or perforated mesh, grid, net or web, defining numerous openings which can be expanded or contracted as will become evident.

One end of the sleeve 21 is open and the other end 22 is closed. The closed end 22 includes attachment means in the form of loops 23 formed by doubling back and laterally compressing an end of the sleeve 20 and inserting the compressed end back into the sleeve 20 through an opening in its wall. The doubled-back sleeve 20 is glued in place so as to hold the loop formation.

For use in anchoring umbilical lines, the sleeve 20 preferably measures approximately 1 mm in internal diameter and 200 mm in overall length when at rest, with the loops 23 being around 20 mm in diameter.

A notable characteristic of the sleeve 20 is that its length can readily be varied by axial compression or tension and that this variation in length has a direct and marked effect upon the diameter of the sleeve 20. Elongation causes the sleeve 20 to narrow whereas shortening the sleeve 20 makes it wider. The helically-wound construction promotes this effect as shown in FIGS. 4(a) and 4(b). In these diagrams, the filaments 24 are shown schematically as intersecting hoops, shown edge-on, that lie at mutually opposite and equal angles with respect to the longitudinal axis of the sleeve 20.

In FIG. 4(a), the sleeve 20 is shown in a compressed condition with the filaments 24 bunched up. The filaments 24 lie at a relatively large angle to the longitudinal axis of the sleeve 20, and the transverse diameter of the sleeve 20 is therefore at a maximum. FIG. 4(b), in contrast, shows the sleeve 20 in an elongated condition. In this instance, the filaments 24 lie at a relatively small, more acute angle with respect to the longitudinal axis of the sleeve 20 and hence the transverse diameter of the sleeve 20 is at a minimum. In this elongated and narrow state, the filaments tightly grip a line 25.

With reference now to the series of illustrations in FIGS. 5(a) to 5(l), the sequence of steps involved in using a sleeve 20 to locate an umbilical line 25 will be described.

Figure 5A:
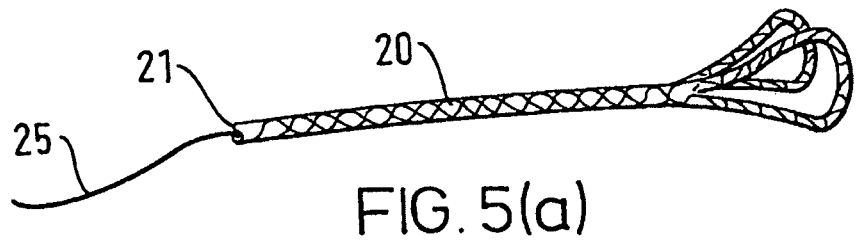
Figure 5B:
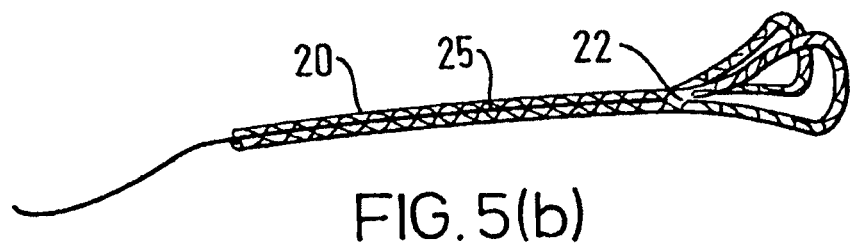

First of all and referring in this regard to FIG. 5(a), an umbilical line 25 is threaded into 20 the open end 21 of the sleeve 20. In FIG. 5(b), the line 25 is shown being fed up the sleeve 20 towards the closed end 22. The progress of the line 25 within the sleeve 20 is eased by gripping the sleeve 20 with the fingers and longitudinally compressing it to shorten it and hence widen its internal diameter. This allows the line 25 to slide freely within the sleeve 20.

Figure 5C:
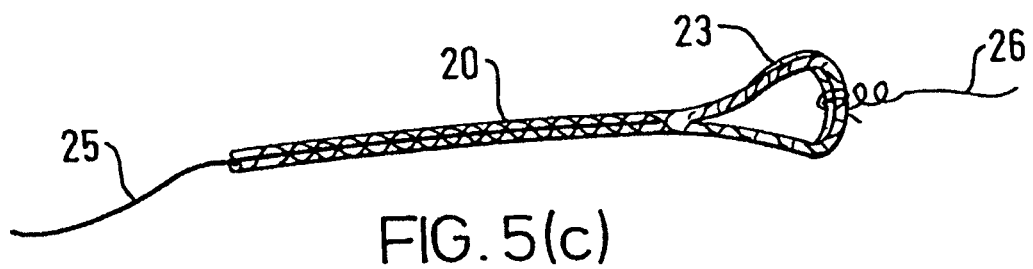
Figure 5D:
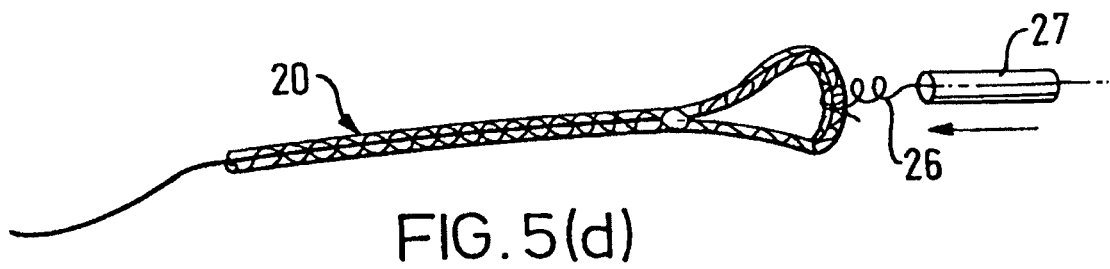
Figure 5E:
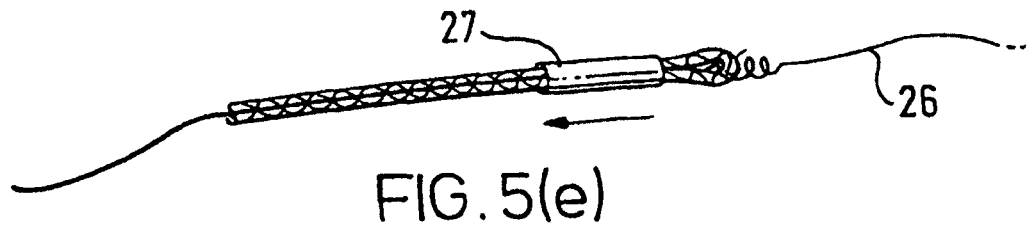
Figure 5F:
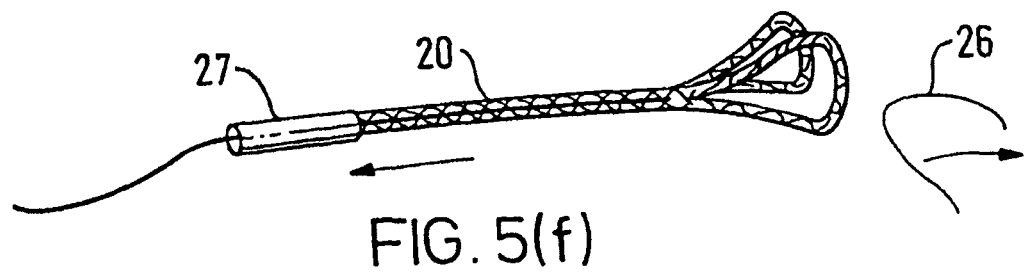

Once the line 25 nears the closed end 22 of the sleeve 20, a monofilament 26 is tied to the pair of loops 23 as shown in FIG. 5(c). Then a silicone rubber collar 27 of about 20 mm in length and 2 mm in diameter is threaded onto the monofilament 26 (FIG. 5(d) and slid along it and over the sleeve 20 (Figure (e)) until it covers the open end 21 of the sleeve 20, at which point the monofilament 26 is untied and discarded (FIG. 5(f). The collar 27 holds together the free ends of the filaments 24 making up the sleeve 20 and so prevents the open end 21 of the sleeve 20 from fraying and unravelling.

Figure 5G:
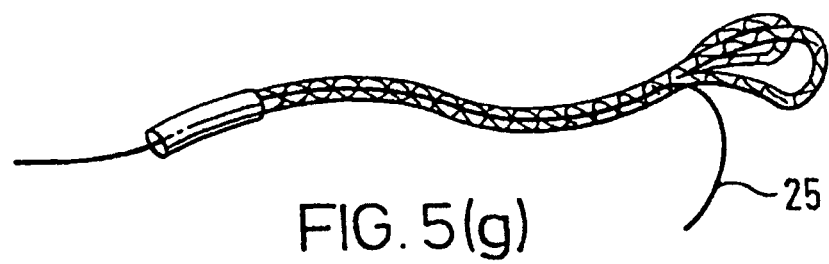
Figure 5H:
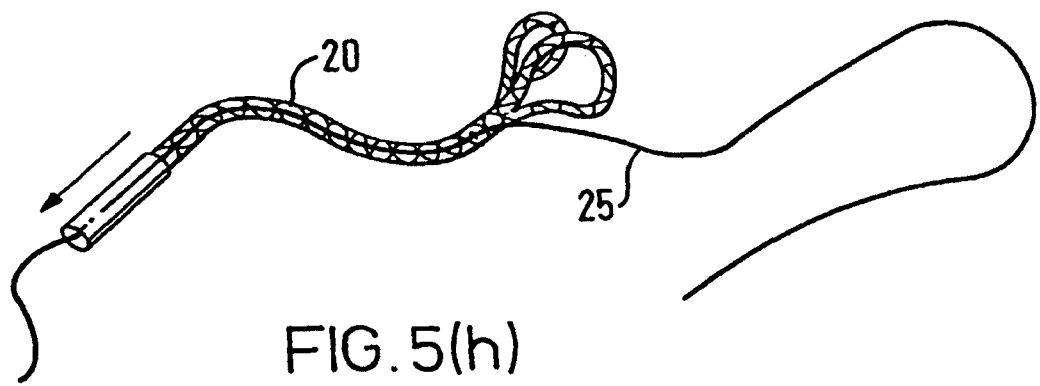

The line 25 is then passed through one of the openings in the sleeve wall (FIG. 5(g) near its closed end 22, following which the sleeve 20 is again longitudinally compressed and slid up along the line 25 pulling through as much line 25 as is required (FIG. 5(h)).

Figure 5I:
Figure 5J:
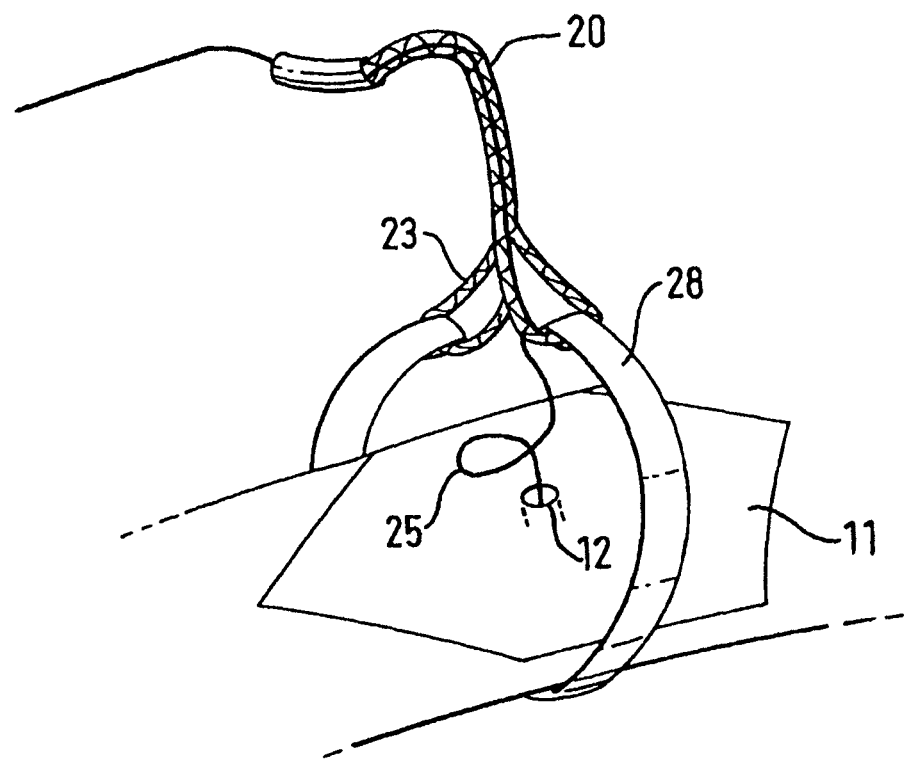

At this stage, the line 25 is ready to be introduced into the umbilicus 12 of a premature infant 11 as shown in FIGS. 5(i) and 5(j). Once the line 25 has been inserted into the umbilicus 12 and its position correctly located, the line 25 is sutured to the umbilicus 12. A harness 28 is passed around the baby's abdomen and attached to the loops 23 of the sleeve 20 as shown in FIG. 5(j). The harness 28 will be described in more detail below with reference to FIG. 6. It is also possible to attach the sleeve 20 directly to the umbilical stump, preferably by suturing.

Figure 5K:
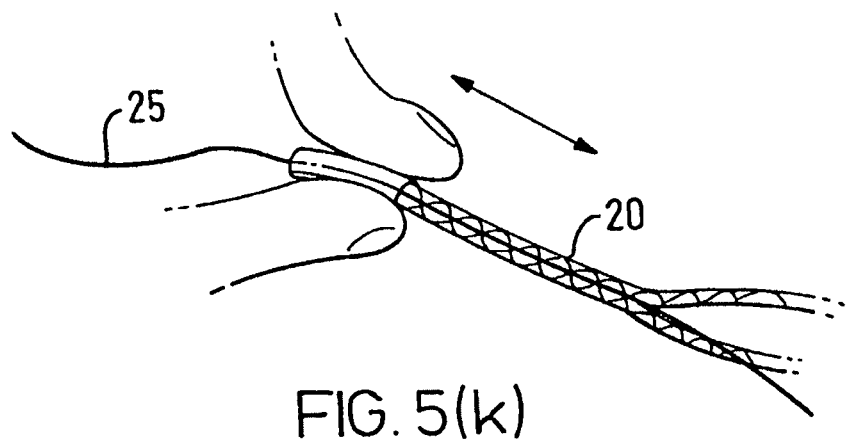

Final adjustments to the line 25 are made and then the sleeve 20 is ready to be locked to the line 25. This is achieved by tensioning the sleeve 20 by pulling it over the line 25 as shown In FIG. 5(k) to elongate and narrow it. In doing so, the helically woven filaments frictionally engage the line 25, collectively imparting an evenly distributed and firm but gentle compressive gripping force over a large area of the line 25. This ensures that the 20 line 25 is secured without restricting its lumen, as could happen if a point or edge loading were applied to the line 25.

The gripping force exerted by the sleeve 20 naturally increases the frictional forces that resist axial movement of the line 25 with respect to the sleeve 20. Moreover, once the compressive and hence frictional forces rise above a certain threshold, it will be clear that further attempts to move the line 25 axially with respect to the sleeve 20 will meet with increased compression and frictional forces that tend to resist the movement ever more strongly without allowing further slippage. This gives rise to a locking effect.

Release of the line 25 is possible simply by longitudinally compressing the sleeve 20 to expand it away from the line 25, thereby allowing adjustments to be made by sliding the line 25 within the sleeve 20. The line 25 can be locked again when desired.

Figure 5L:
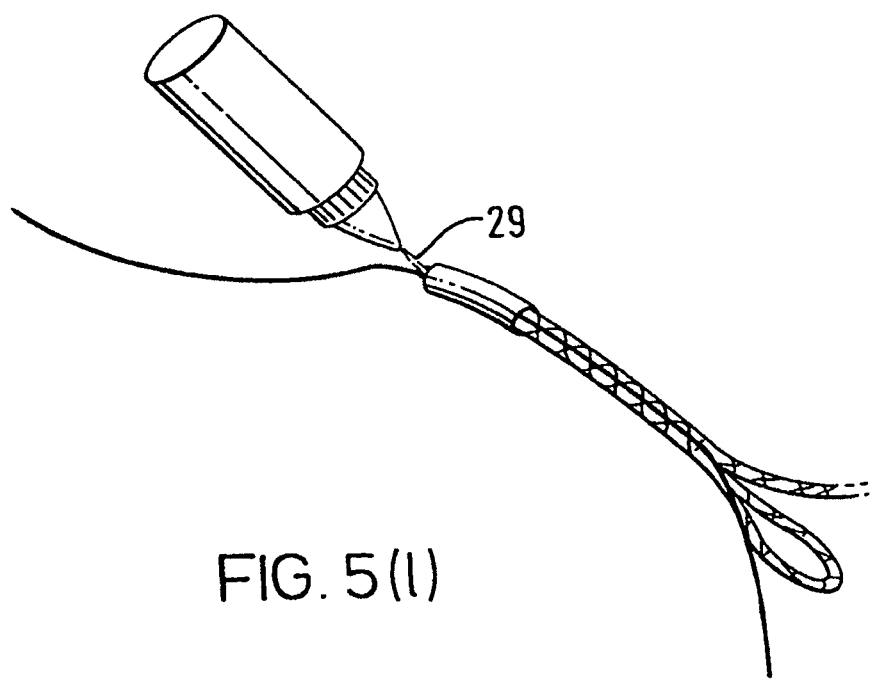

It has been found during testing that the line 25 will break—under loads far in excess of anything encountered in normal use—rather than slip within the sleeve 20 once locked in this way. Nevertheless, in a final optional step, permanent fixing of the sleeve 20 in relation to the line 25 can be achieved by applying medical super glue 29 such as Braun Hystoacryl (trade mark) between the sleeve 20 and the line 25 as shown in FIG. 5(l).

Referring now to FIG. 6 of the drawings, the harness 28 shown in FIG. 50) is an 10 elongate strip of foam Velcro material including a relatively wide central section 30 extending smoothly into relatively narrow opposed ends 31. Each end 31 bas a patch 32 of Velcro material capable of gripping the material from which the remainder of the harness 28 is made.

In use when securing a sleeve 20 to a patient, the ends 31 of the harness 28 are passed 15 through respective loops 23 of the sleeve 20 and are doubled back and secured to the remainder of the harness 28, thereby creating a loop interlocking with each loop 23 of the sleeve 20. The harness 28 passes around the patient's body or part thereof, with the wide central section 30 spreading contact loads and hence promoting comfort while resisting slippage.

If necessary, frictional contact between the harness 28 and the patient may be supplemented by exposing the adhesive surface of an adhesive section 33 located centrally within the central section 30 of the harness 28 and using this to adhesively secure the harness 28 to the patient. Advantageously, the adhesive section 33 has a multi-part peel-off cover allowing a variable proportion of the adhesive surface to be exposed, thereby allowing the minimum practical adhesive contact with the patient's skin as the loads of use may allow.

FIG. 7 illustrates an adhesive tab 34 which functionally and structurally is akin to one half of the harness 28 shown in FIG. 6. The tab 34 is generally spoon-shaped in plan, having a relatively wide end 35 and a relatively narrow end 36. The wide end 35 has an enlarged adhesive section 37 and the narrow end 36 has a Velcro patch 38 capable of forming a loop interlocking with the loop 23 of a sleeve 20. The adhesive section 37 is used to attach the tab 34 to a patient's skin. Two or more such tabs 34 are preferably used, as shown in FIG. 8 which shows the invention applied to a line 25 sited for venous access in a patient's wrist using a Venflon (trade mark) terminal 39. A simple Velcro harness could also be used.

Referring now to FIG. 9, a collar 40 constructed in accordance with the invention is broadly the same as the collar 16 shown in use in FIG. 2. The exceptions are:

an internal sleeve 41 of the same mesh construction as the sleeve 20 shown in FIGS. 3, 4(a) and 4(b);

bias means in the form of a coil compression spring 42 coaxial with and acting upon the sleeve 41 to elongate the sleeve 41; and levers in the form of finger tabs 43, one fixed to the collar 40 at one end of the sleeve 41 and the other attached to and movable with the other end of the sleeve 41 whereby the sleeve can be longitudinally compressed against the force of the spring 42 by squeezing the movable finger tab 43 towards the fixed finger tab 43.

As best shown in FIGS. 10(a), 10(b) and 10(c), the spring 42 bears against rings 44 attached to respective ends of the sleeve 41. One ring 44 is fixed to the collar 40 and the other ring 44 is movable with respect to the collar 40, the movable finger tab 43 conveniently being attached to or integral with the movable ring 44. Although not shown in FIG. 10(a), 10(b) or 10(c), the movable finger tab 43 travels in a slot 45 provided in the collar 40 as shown in FIG. 9.

FIG. 10(a) shows the sleeve 41 at the maximum extension permitted by the collar 40. Biasing means can be used in other arrangements that embody the invention. For example, FIGS. 11(a) and 11(b) illustrate a fastener 46 employing a generally oblong pad 47 for attachment to a patient 48 by adhesive or other suitable means, the pad 47 having a central circular aperture 49, best shown in FIG. 11(a), to admit the line in the form of a catheter or drain 50 shown in FIG. 11(b). A biasing means in the form of a coil spring 51 is attached at one end to the pad 47, concentrically about the aperture 49. Similarly, one end of a sleeve 52 is attached to the pad 47, concentrically about the aperture 49 and within the spring 51. The sleeve 52 extends within the spring 51 and is attached at its other end to a free end of the spring 51, so as to expand and contract with the spring 51.

When the fastener 46 is in use attached to the patient 48 and it is desired to admit a line 50 to the fastener 46, the sleeve 52 is longitudinally compressed and hence widened by pressing the free end of the spring 51 towards the patient 48. When the line 50 has been slid within the sleeve 52 to be positioned where desired, the spring 51 is released: this causes the sleeve 52 to lengthen and contract about the line 50. The end of the spring 51 can also be pulled, further to tighten the grip of the sleeve 52 on the line 50.

FIG. 12 illustrates a fastener 53 being an embodiment of the invention akin to that of FIGS. 11(a) and 11(b); hence, like numerals relate to like parts. In this instance, it will be noted that the spring 51 has been omitted, leaving the sleeve 52 attached to the pad 47 concentrically about the aperture 49 as before, but otherwise unsupported except for a ring 44 at its free end akin to that shown in FIGS. 10(a), 10(b) and 10(c). The effect of this simplification is to require the free end of the sleeve 52 to be pulled manually away from the pad 47 when it is desired to grip a line 50 extending within the sleeve 52 and through the aperture 49, with the fastener 53 in use secured to a patient.

Advantageously, the pad 47 of FIGS. 11(a), 11(b) and 12 can be cut to any desired shape or size.

It has been mentioned that the embodiments of FIGS. 11(a), 11(b) and 12 can be attached to a patient by means other than adhesives and FIGS. 13 and 14 illustrate embodiments adapted for non-adhesive attachment. Specifically, in FIG. 13, the adhesive pad 47 is replaced by an annular flare or flange 54 of material, such as woven nylon fabric, for suturing the fastener to a patient and, in FIG. 14, the flare or flange 54 of material is replaced by loops 55 for securing the fastener to a patient by means of a harness or other separate fastening means that are not shown in FIG. 14. In both cases the fastener is shown as including a spring 51 but this can be omitted in the manner of the simplified embodiment of FIG. 12.

It is also possible for the sleeve of the invention to be supported for extension and contraction by movable means other than a spring or other biasing means. For example, movable means acting on the sleeve can be held by holding means when the sleeve is extended, as shown in FIGS. 15(a) and 15(b).

In this instance, the movable means comprises a first ring 55 supporting one end of a sleeve 56 and a second ring 57 supporting the other end of the sleeve 56, the rings 55, 57 holding open the respective ends of the sleeve 56 and being aligned with one another to hold the sleeve 56 between them as a generally straight tube. The rings 55, 57 are movable in mutual alignment in a straight line towards and away from one another along the longitudinal axis of the tubular sleeve 56. To this end, the second ring 57 is guided in that movement by a threaded rod 58 that is parallel to the longitudinal axis of the sleeve 56, and is caused to move along the rod 58 by nuts 59, 60 threaded onto the rod 58. Accordingly, the second ring 57 can be likened to a carriage and the rod 58 can be likened 20 to a track.

Specifically, the rod 58 is fixed at one end to a leg 61 depending from the first ring 55 and extends through a collar 62 depending from the second ring 57, the collar 62 being a sliding fit over the rod 58. The collar 62 is moved along the rod 58 and held in a desired position by the nuts 59, 60 threaded onto the rod 58, which are disposed one on each side of the collar 62.

The collar 62 can be moved along the rod 58 by turning the nuts 59, 60 in unison and then locked to the rod 58 by contra-rotating the nuts 59, 60 to advance the nuts 59, 60 toward one another. Alternatively, the collar 62 can be moved manually by contra-rotating the nuts 59, 60 to move them apart, providing room for pulling the rings 55, 57 apart by grasping them to extend the sleeve 56 to a desired extent. The sleeve 56 can then be held in its extended state by advancing at least the inner nut 59 into abutment with the collar 62, thus holding the extension of the sleeve 56 against its resilience which tends to shorten the sleeve 56. For optimum location and locking, however, both nuts 59, 60 should be contra-rotated towards each other to advance them into abutment with the collar 62.

A counterpart to the supporting belt 63, such as a shoulder strap, could of course be used to secure a fastener to another part of the patient's body.

Referring now to FIGS. 16(a) and 16(b), it will be seen how a supporting belt 63 around a patient's torso 64 can secure the fastener of the invention. FIG. 16(a) shows a fastener 65 holding a urinary catheter 66, and therefore depending by a strap 67 from the belt 63 to lie just below the patient's groin. FIG. 16(b), on the other hand, shows a fastener 68 holding an epidural line 69 for delivery of drugs to the patient's spinal anatomy. To this end, the fastener 68 is secured to the patient's lower back 64 by loops 70 in the fastener 68 that pass around or are otherwise attached to the belt 63. It will be noted in this instance that the point of entry of the epidural line 69 into the patient's body 64 is covered by an adhesive dressing 71 in the usual manner.

Referring finally to FIGS. 17(a) and 17(b), the openings in the wall of a sleeve 72 can be exploited by passing a line 73 out of the sleeve 72 and back in again to create one or more loops 74 for fastening purposes. The open loops 74 of FIG. 11(a) can be closed up as shown in FIG. 11(b) merely by sliding together the ends of the sleeve 72 along the line 73.

Whilst most lines attached to a patient will be tubes, it is possible that non-tubular lines such as wires for sensing purposes could be attached to a patient by means of the invention.

In embodiments employing movable means to support and extend or shorten the sleeve, guide means other than a threaded rod and holding means other than nuts could be used. An example is an arrangement in which a carriage supporting one end of a sleeve is movable on a track or frame that supports the other end of the sleeve, the carriage being lockable in a desired position by holding means such as a detent, a latch, a ratchet or a clamp acting on the track or frame.

Many other variations are possible without departing from the inventive concept. For example, it is envisaged that the invention could be used to secure lines in any patient when traditional methods of taping or suturing are compromised by conditions such as burns, plaster casts dermatological problems and so on.

The invention could be of particular use in veterinary work for securing lines in animals, where fur, scales or feathers preclude traditional methods.

In general, the invention is not confined by particular material choices or by other selections: many plastics other than nylon can be used and non-plastics such as metallic filaments are possible, as are bias means other than coil compression springs.

Indeed, the present invention may be embodied in many other specific forms without departing from its essential attributes. Accordingly, reference should be made to the appended claims and other general statements herein rather than to the foregoing specific description as indicating the scope of the invention.

The invention claimed is:

1. A medical or surgical apparatus comprising:
   a sterile tube for supplying a fluid to or removing a fluid from a patient; and
   a sterile braided tubular sleeve comprising a substantially rigid ring at each end of the sleeve, the sleeve coupled to the tube such that the tube extends through the sleeve and each ring;
   where the sleeve is configured such that pushing the rings towards each other along the longitudinal axis of the sleeve shortens and widens the sleeve, allowing the sleeve to slide along the tube; and
   where the rings are biased away from each other such that if the rings are released the sleeve will lengthen and grip the tube.

2. The apparatus of claim 1, where the sleeve comprises one or more material selected from the group consisting of nylon, plastic, and metal.

3. The apparatus of claim 1, where one of the rings is configured to be coupled to a patient.

4. The apparatus of claim 3, further comprising: a pad coupled to the one of the rings configured to be coupled to a patient, the pad configured to be coupled to a patient.

5. The apparatus of claim 4, where the pad is configured to be sutured to a patient.

6. The apparatus of claim 4, where the pad comprises adhesive configured to adhere the pad to a patient.

7. The apparatus of claim 3, where the one of the rings configured to be coupled to a patient includes one or more secondary rings configured to be sutured to the patient.

8. The apparatus of claim 1, where the sleeve is configured to bias the rings away from each other.

9. The apparatus of claim 1, further comprising:
   a spring disposed over the sleeve and coupled to each of the rings, such that the spring biases the rings away from each other.

10. The apparatus of claim 1, where at least one ring is coupled to a collar.

11. The apparatus of claim 10, where the collar comprises a support body.

12. The apparatus of claim 10, where the collar is configured to be coupled to a patient.

13. A method of forming a medical or surgical apparatus comprising:
    providing sterile a tube for supplying a fluid to or removing a fluid from a patient;
    coupling an apparatus, comprising a sterile braided tubular sleeve and a substantially rigid ring at each end of the sleeve, to the tube such that the tube extends through the sleeve, where the sleeve is configured such that the rings are biased in opposite directions such that if the rings are released the sleeve will lengthen and grip the tube;
    where coupling comprises: pushing the rings towards each other to shorten and widen the sleeve; passing the tube through the apparatus such that the tube extends through the sleeve and each ring; and releasing the rings to permit the sleeve to return to a biased elongate configuration in which the sleeve grips the tube.

14. The method of claim 13, where the sleeve comprises one or more material selected from the group consisting of nylon, plastic, and metal.

15. The method of claim 13, where one of the rings is configured to be coupled to a patient.

16. The method of claim 15, where the sleeve further comprises:
    a pad coupled to the one of the rings configured to be coupled to a patient, the pad configured to be coupled to a patient.

17. The method of claim 16, where the pad is configured to be sutured to a patient.

18. The method of claim 16, where the pad comprises adhesive configured to adhere the pad to a patient.

19. The method of claim 15, where the one of the rings configured to be coupled to a patient includes one or more secondary rings configured to be sutured to the patient.

20. The method of claim 13, where the sleeve is configured to bias the rings away from each other.

21. The method of claim 13, where the sleeve further comprises:
    a spring disposed over the sleeve and coupled to each of the rings, such that the spring biases the rings away from each other.

* * * * *

UNITED STATES PATENT AND TRADEMARK OFFICE
CERTIFICATE OF CORRECTION

PATENT NO. : 8,435,216 B2
APPLICATION NO. : 12/838236
DATED : May 7, 2013
INVENTOR(S) : Marc Howard Spinoza Page 1 of 1

It is certified that error appears in the above-identified patent and that said Letters Patent is hereby corrected as shown below:

In the Claims:

In claim 13, column 12, line 28, delete "sterile a" and insert --a sterile-- therefor.

Signed and Sealed this
Eleventh Day of June, 2013

Teresa Stanek Rea
*Acting Director of the United States Patent and Trademark Office*